United States Patent [19]
Karram et al.

[11] Patent Number: 6,095,969
[45] Date of Patent: Aug. 1, 2000

[54] FEMALE INCONTINENCE CONTROL DEVICE ACTUATED BY ABDOMINAL PRESSURE

[76] Inventors: Mickey M. Karram, 8000 Indian Hill Rd., Cincinnati, Ohio 45243; Bryan D. Knodel, 6100 N. Country Club, Flagstaff, Ariz. 86004

[21] Appl. No.: 09/033,242

[22] Filed: Mar. 3, 1998

[51] Int. Cl.⁷ .................................. A61F 2/00; A61F 2/02
[52] U.S. Cl. .................................. 600/31; 600/29; 600/30
[58] Field of Search .................................. 600/29, 30, 31

[56] References Cited

U.S. PATENT DOCUMENTS

| | | | |
|---|---|---|---|
| 2,455,859 | 12/1948 | Foley | 600/31 |
| 3,750,194 | 8/1973 | Summers | 600/31 |
| 4,222,377 | 9/1980 | Burton | 600/31 |
| 4,682,583 | 7/1987 | Burton et al. | 600/30 |
| 5,478,305 | 12/1995 | Craggs | 600/31 |
| 5,634,878 | 6/1997 | Grundei et al. | 600/30 |

Primary Examiner—Cary O'Connor
Assistant Examiner—Navin Natnithithadha
Attorney, Agent, or Firm—Chittaranjan N. Nirmel; Jones Jain, L.L.P.

[57] ABSTRACT

A surgeon-implantable, fluid-filled, flexible device for automatically controlling stress incontinence in female patients employs a flexible diaphragm element positioned in the patient's abdominal space to compress in response to increases in intraabdominal pressure. Upon such compression of the diaphragm, pressurized fluid flows therefrom via a flexible tubing, optionally via a flow control element, to an inflatable urethra-constricting element in fluid communication therewith and positioned over the patient's urethra close to her bladder neck. Thus, when the patient experiences an increase in intraabdominal pressure, e.g., when she coughs, fluid from the diaphragm flows rapidly to the urethra-constricting element which presses against and forcibly constricts the urethra adjacent thereto. Upon abatement of the intraabdominal pressure, the flow control element releases fluid from the urethra-constricting element which then ceases to press on the urethra.

32 Claims, 5 Drawing Sheets

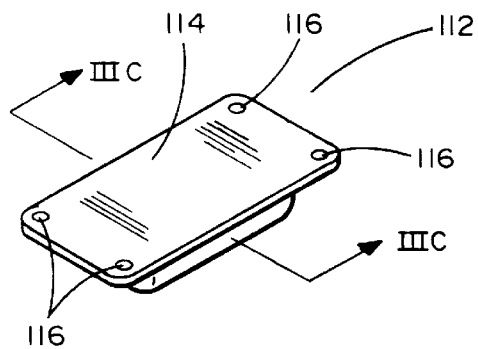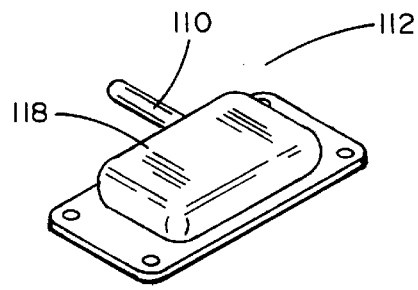
FIG. 3A  FIG. 3B
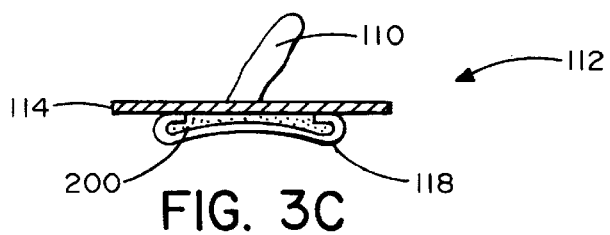
FIG. 3C
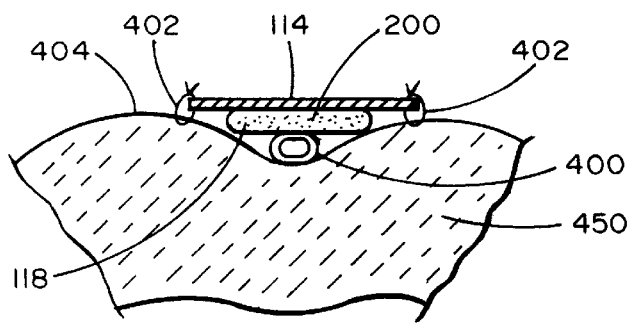
FIG. 4A
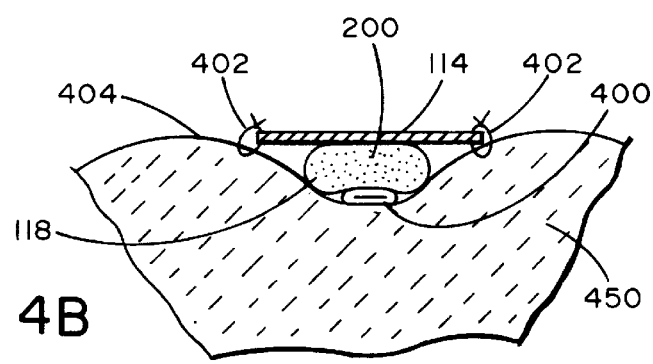
FIG. 4B

FEMALE INCONTINENCE CONTROL DEVICE ACTUATED BY ABDOMINAL PRESSURE

FIELD OF THE INVENTION

This invention relates to apparatus and a method for controlling female stress-induced incontinence. More particularly, it relates to apparatus provided within a female user to respond automatically to constrict the user's urethra in response to an increase in abdominal pressure.

BACKGROUND OF THE RELATED ART

Incontinence, i.e., uncontrolled release of urine from the bladder, has been noticed as a condition affecting a growing segment of the female population in the United States. It is believed that, in the U.S., approximately 40% of community-dwelling females over 60 years of age suffer from urinary incontinence that is felt to be socially disabling. See J. Urol., vol. 136, p. 1022, 1986. This also has a huge economic impact on society. A recent estimate of the annual direct costs of caring for persons of all ages with incontinence is about $11.2 billion in the community and about $5.2 billion in nursing homes (based on 1994 dollars). See Geriatric Nephrol. Urol., v. 4, pp.85–91, 1994.

The problems of incontinence in females can be broadly grouped into one of two categories. The first category is one where the incontinence is due to involuntary contraction of the bladder (or detrusor) muscle. Such a condition is sometimes termed "an unstable bladder." The second category is the more common one and comprises stress-induced incontinence, which is best understood as involuntary loss of urine occurring in correspondence with an increase in the female's abdominal pressure, e.g., during a sudden bout of coughing.

Over one hundred surgical/operational procedures, aimed at controlling or obstructing urine flow through the female urethra, have been proposed to alleviate this common problem. The fact that there are so many different surgical procedures proposed is evidence that no single operation has been successful in correcting this condition.

Several devices offering alternatives to surgery are commercially available to provide temporary relief from the problem of female incontinence. These include, for example, the "Artificial Urinary Sphincter", marketed by American Medical Systems; the "Reliance" (intra-urethral plug) and the "Impress" (external urethral patch), both marketed by Uromed; and the "Capture" (also an external urethral patch) marketed by Bard Urologic.

The "Artificial Urinary Sphincter" comprises an inflatable cuff, which is a surgically implanted device which encircles the user's urethra. The cuff is manually deflatable by actuation of a finger-actuated pump placed in the user's labia majora. There are, however, certain limitations in the use of such a device. For example, the cuff is relatively large and cumbersome to install surgically as it requires dissection around the proximal urethra to allow placement of the cuff between the posterior urethra and the anterior vaginal wall. Furthermore, the pump and release mechanism often cannot be comfortably placed in the user's labia majora. During use, this device requires the user's urethra to be continuously obstructed via the inflated cuff and has to be manually released by compressing the pump when voiding is desired. Such devices also have significant technical failure rates. See J. Urol., vol. 136, p.778, 1987. For these reasons, the artificial splincter is rarely implanted in female patients with stress incontinence.

The "Reliance" device is an internal urethra plug which must be inserted by the user into her urethra. Following the insertion, the user employs a syringe to inflate a small balloon at the distal portion of the device which rests at the neck of the user's bladder to thereby obstruct urine flow. When the user needs to void she has to pull on a string at the level of the external urethral meatus which deflates the balloon and permits the user to withdraw the device. A major drawback of such a device is that it is designed to be used as a disposable single-use product. The typical user thus requires numerous devices every day and incurs significant expense. In addition, the device is a temporarily placed, and frequently replaced, foreign body located in a highly sensitive region of the urethra and this may pre-dispose her to urinary tract infections and urethral irritation.

The "Impress" is an external patch which is placed over the opening of the urethra by the user and is held in place by an adhesive. When the user wishes to empty her bladder, she must remove the patch and must replace it with a new patch after voiding. One of the major drawbacks of such a device is leakage of urine around the patch because of insufficient adhesion. In addition, it also has the limitation of being a single-use disposable product, which requires the user to carry a number of the devices with her and incurs significant expense.

The "Capture" is another external device, which is also placed over the opening of the urethra. This device is marketed by Bard Urologic and is somewhat similar to the "Impress" device but remains in place via a suction created during placement of the device. The limitations of such a device include ineffective fixation on to the external urethra, cost, and incovenience due to it's being a single-use disposable product.

As previously mentioned, over a hundred surgical operations have been described to correct female stress incontinence. These operations are aimed at elevating and/or stabilizing the urethrovesical junction or partially obstructing the urethra. Since so many operations have been described, obviously no single operation has been successful in completely eradicating this condition. The difficulty revolves around the fact that there is no standard technique for determining the amount of tension to be placed on sutures or sling material. Also, significant complication rates have been reported. See "Clinical Practice Guidelines for Urinary Incontinence in Adults: Acute, and Chronic Management", No. 2, 1996 Update, pp. 53–59, published by the U.S. Dept. of Health and Human Services, Agency for Health Care Policy and Research.

Accordingly, there is a present and significant need for a device and a method of providing protection against the inconvenience of stress-induced incontinence which would be automatically actuated only when the female user experiences a rise in abdominal pressure, of sufficient magnitude to produce leakage.

SUMMARY OF THE INVENTION

Accordingly, a principal object of this invention is to provide a device which can be implanted into a female user to apply constriction to her urethra at an optimum location automatically, i.e., without voluntary action on her part, whenever she experiences elevated abdominal pressure, with the constriction being automatically released when the abdominal pressure is relieved.

A related object of this invention is to provide an internally contained device wearable by a female user to prevent involuntary incontinence under circumstances which cause her to experience elevated abdominal pressure.

Yet another object of this invention is to provide an internally worn device which protects a female user against stress-induced incontinence, the device being capable of automatically acting to constrict her urethra whenever she suffers elevated abdominal pressure and automatically acts to gradually release control over the urethra when the abdominal pressure abates.

It is an even further object of this invention to provide a method by which a female user can employ an internally worn device to automatically constrict her urethra to prevent stress-induced incontinence in a manner such that control over the urethra is released without action on her part when her abdominal pressure abates.

It is a related object of this invention to provide a method by which a female user may internally wear a device in such a manner as to automatically constrict her urethra to prevent stress-induced incontinence and gradually release control over the urethra when incontinence-inducing stress abates.

These and other related objects of this invention are realized by providing an apparatus for controlling female incontinence, which comprises an inflatable element compressible in response to ambient pressure increase and having a first opening, a length of flexible tubing communicating at a first end with an interior of the inflatable element via said first opening, and a urethra-constricting element which has an inflatable portion with a second opening communicating with a second end of said flexible tubing.

In another aspect of this invention there is provided a method for preventing stress-induced incontinence, comprising the steps of forming a small transverse skin incision above the symphysis pubis of a female patient and then entering the patient's retropubic space in known manner and identifying an anatomic location of the bladder neck of the patient. This is followed by the step of fixing to the patient's vagina, on opposite sides of the proximal urethra and bladder neck, a urethra-constricting element comprising an inflatable portion communicating with one end of a length of flexible tubing; and, in communication with another end of said tubing, providing an inflatable element that is compressible in response to ambient pressure increase and is placed at a selected location in the abdomen such that when the inflatable element is subjected to an increase in intraabdominal pressure it will compress to transfer a fluid via said tubing to expand the inflatable portion of the urethra-constricting element against an immediately adjacent portion of the urethra to thereby squeeze and locally constrict the urethra.

In yet another aspect of this invention, there is provided a method of controlling female incontinence, which includes the steps of insufflating a female patient's abdomen with carbon dioxide, forming a sharp or blunt entrance into the patient's retropubic space with laparoscopic scissors or any other known instrument, and identifying the patient's bladder neck. This is followed by the step of placing in the retropubic space an inflatable element communicating via a flexible tubing with a urethra-constricting element having an inflatable portion positioned over a selected portion of the patient's urethra, whereby an increase in the patient's abdominal pressure will cause compression of the inflatable element, transmission of pressure via the tubing, and a corresponding expansion of the inflatable portion of the urethra-constricting element to press against an adjacent portion of the patient's urethra and squeeze the same to impede urine flow therethrough.

BRIEF DESCRIPTION OF THE DRAWING

FIG. 3A is a first perspective view of an exemplary inflatable urethra-compressing component, fitted to a substantially planar base, in the device according to the first embodiment per FIG. 1; FIG. 3B is a perspective view of the same urethra-compressing component from an opposite side; and FIG. 3C is a cross-sectional view at Section IIIC—IIIC in FIG. 3A.

FIG. 4A is a schematic transverse cross-sectional view of the urethra-constricting component per FIGS. 3A—3C, in installed position relative to an optimum location on the urethra, in an uninflated state; and FIG. 4B is a similar view of the same device when it is inflated to constrict the urethra.

DETAILED DESCRIPTION OF THE PREFERRED EMBODIMENTS

Figure 1:
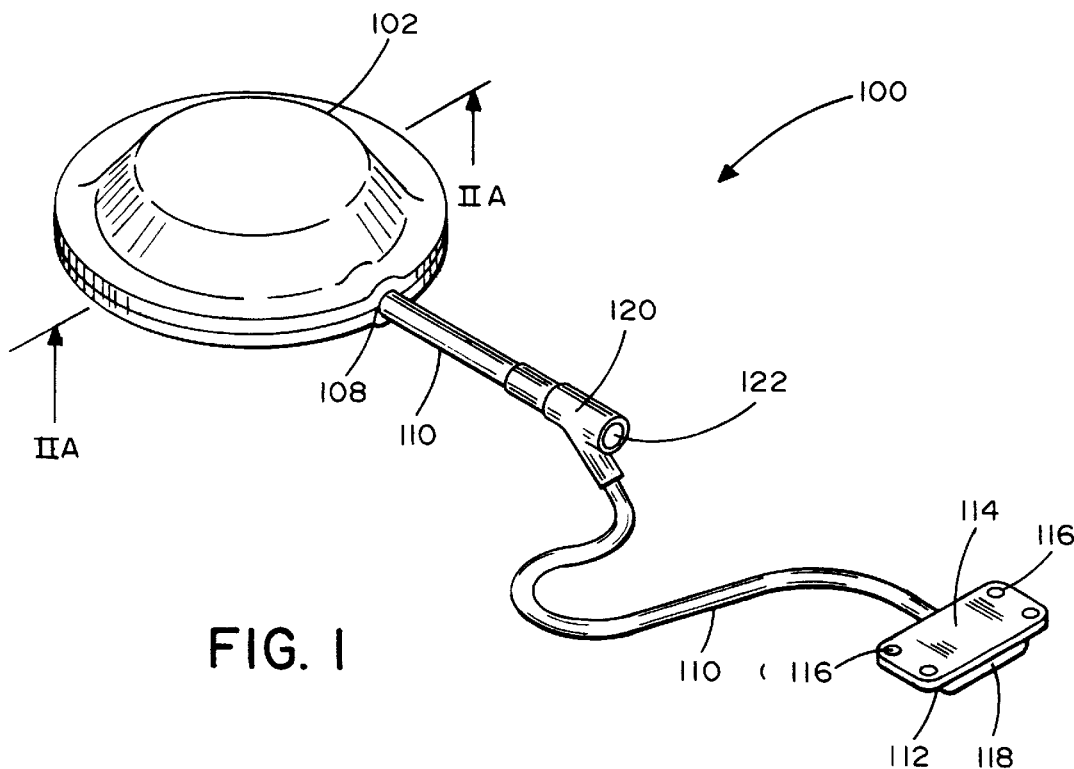
FIG. 1 is a perspective view of a first preferred embodiment of this invention.

As best seen in FIG. 1, in a first preferred embodiment of this invention there is provided an incontinence control device 100 which comprises at a first end a flexible, pressure-sensitive, hollow, diaphragm component 102 having a deformable interior space.

Figure 2A:
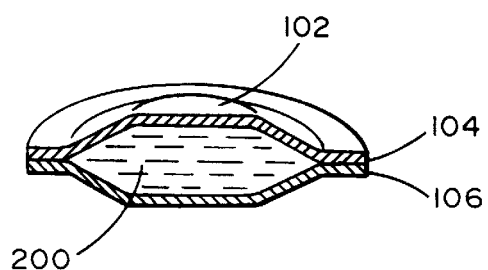
FIG. 2A is a transverse cross-sectional view of a controllably inflatable, flexible, pressure-responsive, diaphragm component of the apparatus at Section IIA—IIA in the first embodiment per FIG. 1, in a relatively inflated state.

As best seen in FIG. 2(A), diaphragm 102 is most conveniently formed of two flexible sheet-like elements 104 and 106 adhered around their respective annular portions to each other. A substantial portion of the central area of each of elements 104 and 106 is left unadhered to the other, so that when a biocompatible fluid 200 is provided therein there is formed a space of variable volume filled with the fluid 200.

The material of which elements 104 and 106 are made is chosen from well-known flexible, durable, sterilizable, biocompatible materials. These typically are plastics materials which can be sterilized in conventional manner, e.g., in an autoclave or otherwise during or after manufacture, are relatively inexpensive, and can be securely adhered to each other with conventional adherent materials or heat-seamed to each other by the application of a localized high temperature in known manner. The exact compositions of these materials, and the ways in which they may be joined or adhered to each other, are not critical to this invention and any conventional technique may be employed to form the structure of diaphragm 102.

Diaphragm 102 communicates at an opening 108 with a first end of a flexible, biocompatible tubing 110 which may be of an overall length selected by the prescribing surgeon, i.e., this is an element having a longitudinal dimension customized to suit the user. In the alternative, the device 100 can be made in modular fashion, for example with various lengths of the flexible tubing element 110, so that a prescribing surgeon may simply select the structure most appropriate for a particular patient.

At the other end of flexible tubing 110, and in fluid communication therewith, there is provided a urethra-constricting unit 112 having a substantially rigid base 114 which may be but is not necessarily flat. Base 114 is preferably provided with a plurality of through-holes 116 close to its edges, preferably near its corners if it is selected to be of a substantially rectangular shape. It is not necessary that it be of rectangular shape, have a specific number of through-holes 116, or have a specific thickness. These are all matters of design choice. What is important is that base 114 be made of a size and shape suitable for secure long-term affixation by known means to the user's tissue as described below.

As best seen in FIG. 2A, an exemplary diaphragm 102 may be of two cooperating flexible elements 104 and 106 connected to each other in a peripheral annular interface region, so that a substantially central portion may be flexibly spaced-apart by increasing the amount of a fluid 200 contained in the space therebetween. Obviously, using suitable manufacturing techniques, such a component may be made to have a unitary structure, e.g., like a bladder having a single opening at which it communicates with a proximal end of tubing 110. The fluid 200 should be a sterile, biocompatible liquid, e.g., a saline solution, which can do no harm to the patient in the event of a system rupture leading to uncontrolled release of the fluid into the patient's abdomen.

For certain applications, e.g., when the surgeon concludes that the patient would be best served by laparoscopic implantation of the device, it may be appropriate to fill the device with a suitable fluid after it is implanted as desired. In such a procedure all of the principal elements, i.e., diaphragm 102, tubing 110 and urethra-constricting element 114, are made of flexible materials so that each can be rolled tight to be introduced into the patient's abdominal cavity via a suitable tubular cannula. Then, with the use of conventional laparoscopic forceps, and/or other known tools, the elements may be readily assembled within the patient's abdominal cavity.

To be operational, the system then must be filled with a suitable amount of fluid. To facilitate this step, an additional cannula-insertable valve element 120, e.g., of a kind known for use with intravenous tubing, may be connected to two segments of flexible tubing 110 as best seen in FIG. 1. An example of such a known and commercially available injection valve element is QUOSINA Model No. 84040. Once the assembly is complete, the surgeon forcibly inserts a hypodermic needle into valve 120, via a resilient seal element 122 thereof, to inject the fluid. Upon withdrawal of the needle the seal element closes up and the fluid is thereafter retained within the apparatus to perform its intended function.

Figure 2B:
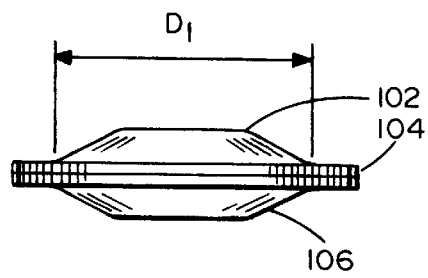
FIG. 2B is a side elevation view of the same diaphragm component in a relatively inflated state.

FIG. 2B shows diaphragm 102 in side elevation view when it contains sufficient fluid 200 to cause a substantial distention of the fluid-containing space defined therein. As will be understood by persons of ordinary skill in the mechanical arts, a selected amount of fluid 200 must be present within diaphragm 102 to cause the substantially central portions of flexible portions 104 and 106 to be spaced-apart from each other to define a relatively large central volume, e.g., in the region having diameter "$D_1$". As described below with reference to FIG. 7, an internal element may be included to ensure an outward biasing force to ensure such spaced-apart central disposition of flexible elements 104 and 106.

When there is a sufficient amount of fluid 200 contained within diaphragm 102, the substantially central portions of flexible portions 104 and 106 will be well spaced-apart and together will present a relatively large external surface area subjected to ambient external pressure changes on both sides. There will be corresponding pressure changes felt by the fluid 200 contained within diaphragm 102 and the flexible tubing 110 and urethra-constricting component 112 that are in fluid communication with each other.

Any pressure increase felt from the ambient surroundings of diaphragm 102 located in the abdominal cavity where it will experience pressure changes, e.g., if the patient coughs, will cause it to be compressed. A corresponding expulsion of a pressurized outward flow of fluid will then be rapidly communicated via flexible tubing element 110 from the diaphragm 102 to cause some fluid from the tubing element 110 to enter into urethra-constricting element 112.

The amount of fluid to be placed in the containment space defined within the diaphragm 102, flexible tubing 110 and inflatable urethra-constricting element 112 can be pre-operatively determined by performing an abdominal leak point pressure test on the patient. This test can quantitate exactly how much abdominal pressure is required to produce leakage in a particular patient, hence on the basis of experience and empirical data the device can be reliably customized by the surgeon to suit the patient's specific needs.

The exact shape of diaphragm 102 is not critical to this invention, i.e., it need not be circular and may even be of irregular shape if deemed advantageous.

As best seen in FIG. 3A, urethra-constricting element 112 has a base 114 provided with a plurality of through-holes 116. To one side of base 114, as best seen in FIG. 3B, is connected a flexible compartment 118 which communicates with flexible tubing 110. As best seen in FIG. 3C, the fluid contained within diaphragm element 102 can communicate any pressure changes through the fluid contained in flexible tubing 110 to the fluid contained within flexible compartment 118. Therefore, when the user's abdominal pressure acting on diaphragm 102 increases, the effect will be transmitted via a corresponding pressurized flow of fluid 200 contained within tubing 110 to the fluid contained in flexible urethra-constricting chamber 118 and this will cause the latter to expand in volume.

The material of which base 114 is made, as well as the material of which flexible chamber 118 is made, are matters of design choice. What is required is that these materials be sterilizable and biocompatible over extended periods. Numerous such materials are known and are commercially used in implant structures, and the specific choice is not critical to the success of this invention.

Figure 11:
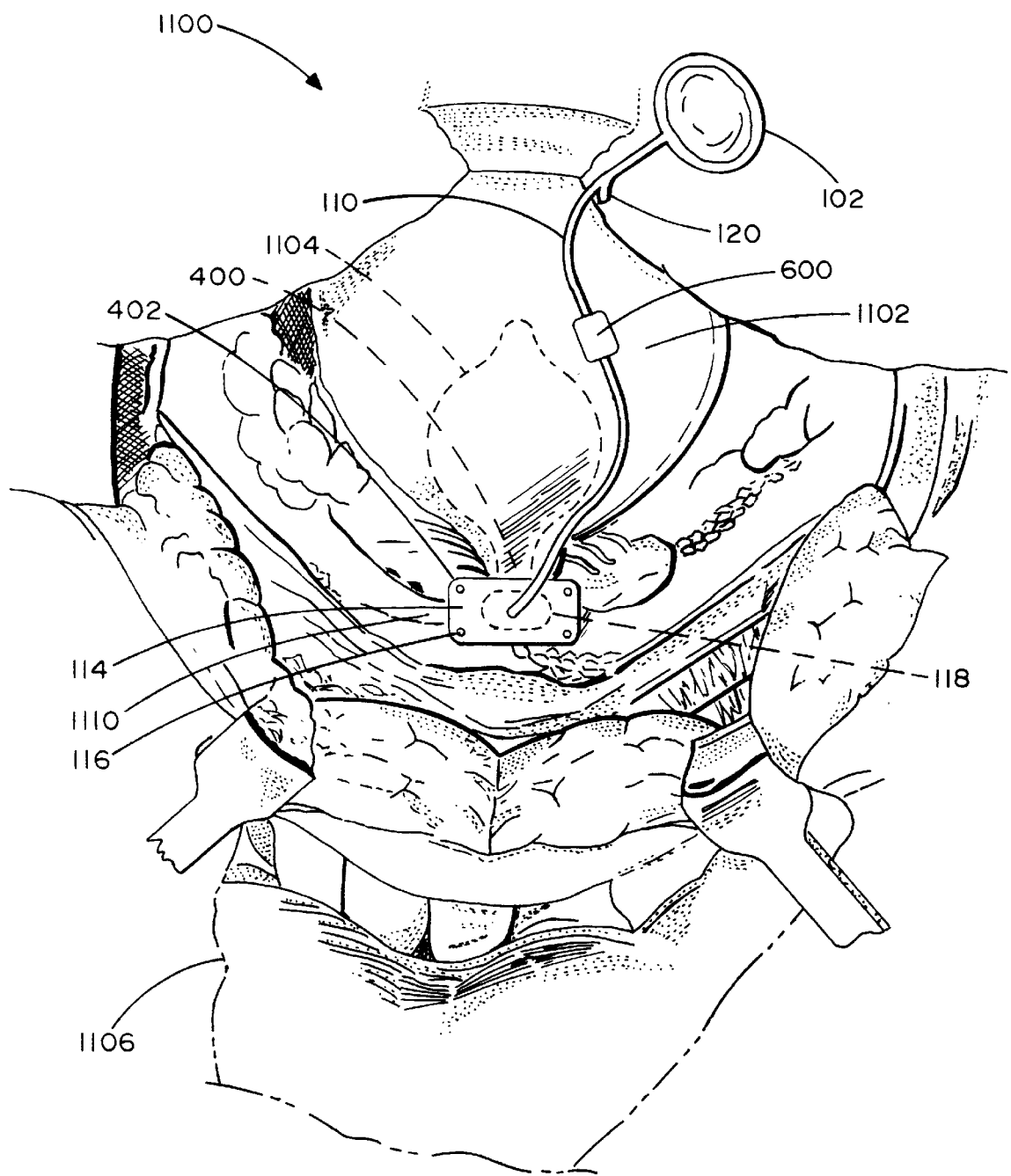
FIG. 11 shows a view of a patient's surgically exposed abdomen with an incontinence device emplaced in accordance with an embodiment of the present invention.

As best seen in FIG. 4A, in its operational position the urethra-constricting element 112 is preferably sutured via through-holes 116, or otherwise securely disposed, over a selected portion of tissue 450 close to the female user's urethra 400. Sutures 402, 402 passing through through-holes 116, 116 preferably anchor the urethra-constricting component 112, as shown in FIGS. 4A and 4B, to the user's anterior vaginal wall and/or to the symphysis pubis 404. Other known alternatives such as clips, staples, screws (into bone), or even selected adhesives may be employed to affix urethra-constricting element 112 in place. See also FIG. 11.

Urethra-constricting element 112 is disposed with its flexible chamber 118 in direct contact with that portion of urethra 400 which is to be pressured and forcibly deformed in response to the fluid flow under pressure transmitted via tubing 110. FIG. 4B schematically illustrates a situation in which, due to a rise in abdominal pressure, as when the female user of the device coughs or sneezes, there is a temporary but swift rise in abdominal pressure experienced by fluid 200 contained in diaphragm element 102. This will lead to pressurized flow of fluid 200 from diaphragm 102 via flexible tubing 110 to the interior of flexible chamber 118 which will correspondingly expand in volume. The portion of flexible chamber 118 which is in direct contact with urethra 400 will thus be inflated and forced to move away from anchored base 114 and toward the urethra so as to squeeze and forcibly close it to prevent flow of urine therethrough.

In simple terms, therefore, when the user of device 100 experiences an increase in abdominal pressure during a natural activity such as coughing or sneezing, she will not experience consequential involuntary stress-incontinence. Instead, the increase in her abdominal pressure will automatically squeeze out some of the fluid 200 contained within diaphragm 102 and send it via flexible tubing 110 to the interior of chamber 118 which will then expand in volume and immediately compress urethra 400 to prevent expulsion of urine from the user's bladder.

The benefits of the first embodiment of this invention may be readily summarized as follows: depending on the age and physical size of the patient, the surgeon installing the first preferred embodiment 100 will select a diaphragm 102 of suitable size, preferably from a modular set of the same. The surgeon will then ensure that there is a suitable length of flexible tubing 110 communicating therewith and with a urethra-constricting element 112 attached, as shown in FIG. 1, with a predetermined quantity of biocompatible fluid 200 filled in. The surgeon will then insert the flexible pressure-sensitive diaphragm into the patient/user's abdomen where it will readily experience changes in ambient abdominal pressure.

If a laparoscopic procedure is selected, the elements will be introduced into patient's abdomen via a cannula, located in assembly with each other, and inflated with a predetermined amount of selected fluid as described earlier.

As will be appreciated, it is important that a sudden increase in the patient's abdominal pressure be communicated rapidly to the urethra-constricting element 112 to cause it to promptly constrict the adjacent portion of the urethra 400, i.e., cause it to go from the state shown in FIG. 4A to the state shown in FIG. 4B. Delay in this action may permit leakage of urine and is to be avoided. On the other hand, it is highly desirable that abatement of the pressure increase not result in an immediate cessation of the closing force being applied to the urethra by urethra-constricting element 112. In other words, it is desirable to provide a mechanism for imposing a time-delay in the release of the constricting force applied to the urethra, so that any residual pressure still experienced by the bladder is not caused to result in involuntary leakage of urine.

Figure 5:
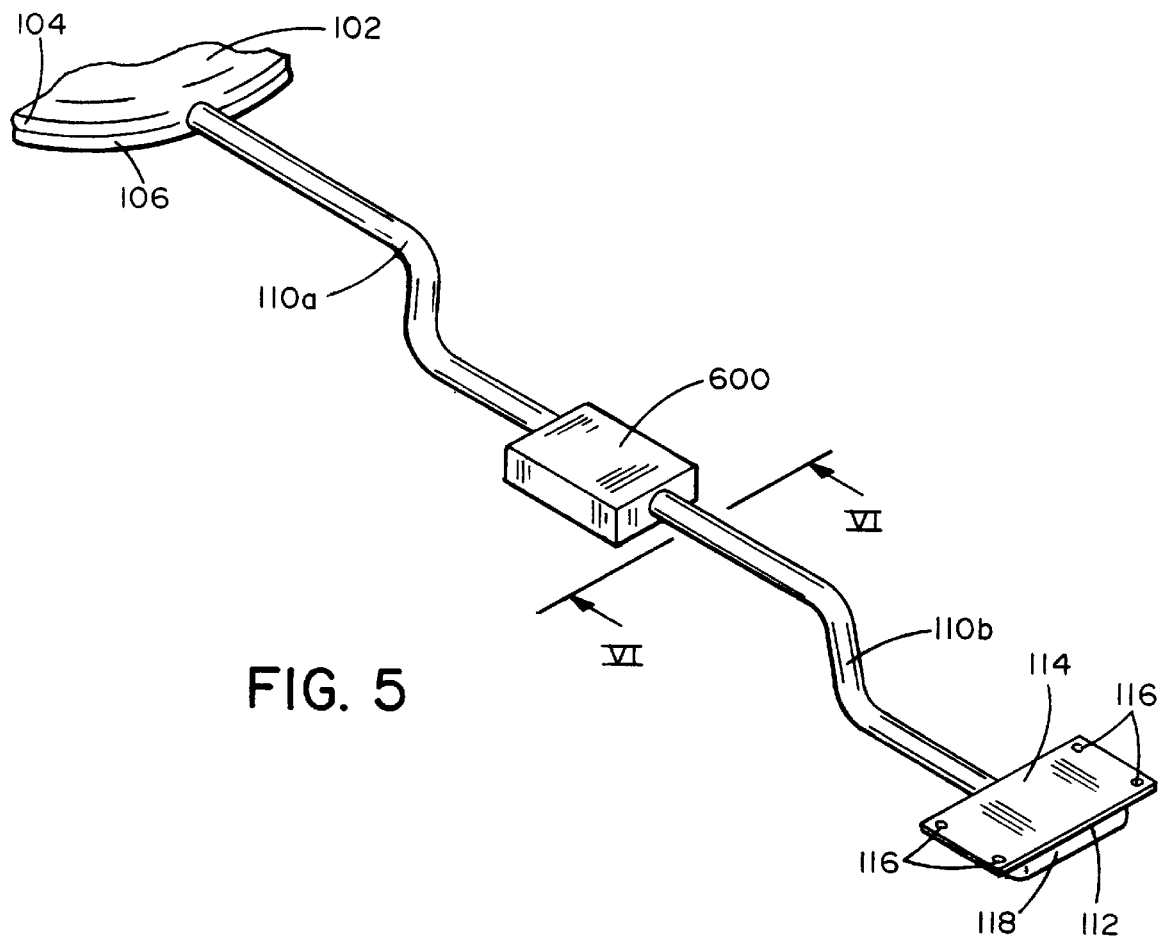
FIG. 5 is a partial perspective view of a second preferred embodiment of the invention, generally similar to the first preferred embodiment but also including a flow-modulating component.

FIG. 5, in schematic form, indicates how a small flow-control element 600 may be included in the system described above. The system as shown in FIG. 5 includes both flow-control element 600 and fluid-injection valve element 120. Persons of ordinary skill in the art will appreciate that either or both of these elements may be included in the system as desired.

Figure 6:
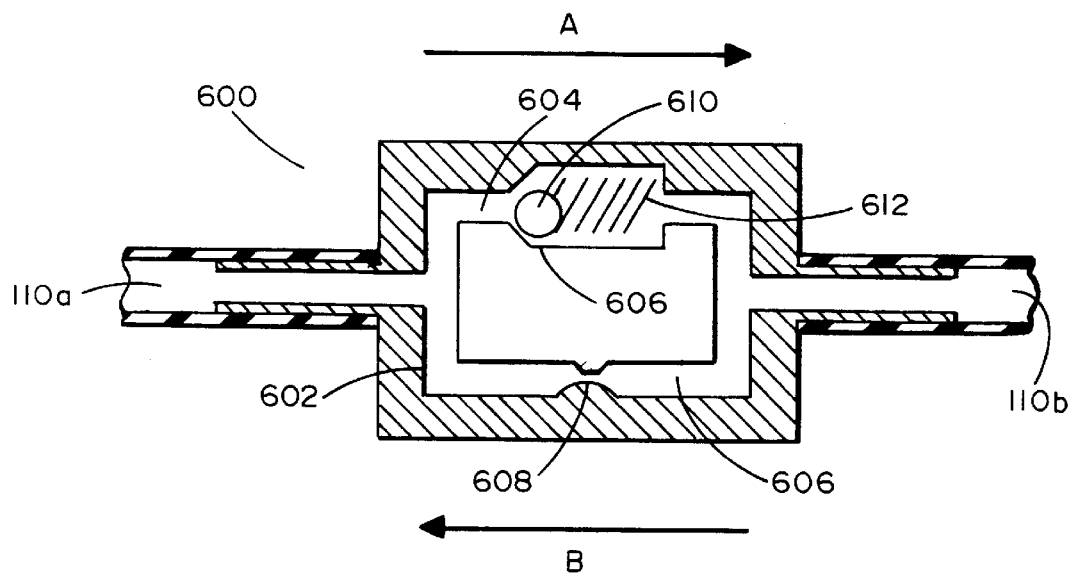
FIG. 6 is a transverse cross-sectional view, at Section VI—VI, of the flow-modulating component of the second embodiment per FIG. 5.

As best seen in transverse cross-sectional view per FIG. 6, flow-control element 600 in exemplary form preferably include a loop-channel 602 communicating at one point with a portion 110a of the flexible tubing connected to diaphragm 102 and, on an opposite side of flow-control element 600, to a length of tubing 110b connected to urethra-constricting element 112.

Loop 602 preferably has a first branch 604 provided with a one-way valve structure 606 such that flow of fluid is permitted only in the direction of arrow "A", i.e., only from diaphragm 102 toward urethra-constricting element 112. Loop 602 also includes a second branch 606 provided with a carefully-calibrated flow-limiting, small-bore, flow-impedance portion 608. In principle, the fluid can flow through flow-impedance portion 608 in both directions, but can do so only at a selected relatively slow flow rate in direction "B".

Flow valve element 606 may comprise, as illustrated in FIG. 6, a conical portion of branch 604, a ball 610, and a helical biasing spring 612 which tends to apply a biasing force to resiliently hold ball 610 in the conical portion of branch 604 to keep it closed. Then, when pressure on the diaphragm side increases sufficiently, the biasing force of spring 612 will be overcome, ball 610 will be forcibly moved out of place, and fluid can flow past the ball so long as a sufficient pressure is available. Some fluid will simultaneously also flow through small-bore flow-impedance portion 608 of the opposite branch 606. The combined flow of fluid will thus flow through both branches 604 and 606 into the urethra-constricting element 112 in direction "A" whenever there is a significant increase in abdominal pressure.

When the abdominal pressure abates, there will be a tendency for fluid from the urethra-constricting element to flow via tubing 110b back through flow control element 600 into diaphragm 102. Upon the abatement of abdominal pressure, spring 612 and ball 610 will cooperate to seal off branch 604 of loop 602. Return flow, in direction B, can now take place solely through small-bore flow-impedance portion 608 of branch 606 of loop 602.

The flow-impedance provided by impedance portion 608 is a matter of design choice, and by appropriate dimensioning it can be expected to slow down release of the force applied to previously constrict urethra 400 for a selected length of time, e.g., by a few seconds. With the provision of such a flow-control element 600, therefore, the system will act promptly in response to sudden increases in abdominal pressure to close off the patients's urethra but, upon the abatement of such a pressure, will take a few seconds to totally remove the force applied to the urethra.

Figure 7:
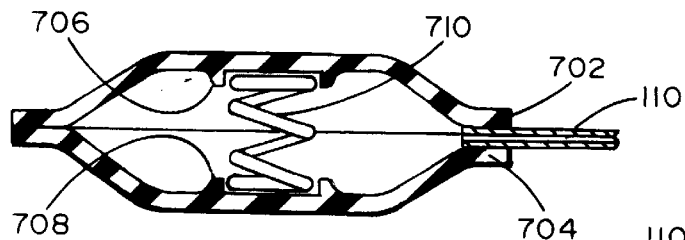
FIG. 7 is a cross-sectional view of a diaphragm provided with an expansion element.

It is desirable that upon the abatement of ambient abdominal pressure diaphragm 102 be refilled with fluid flowing back via tubing 110 from the urethra-constricting element 112. FIG. 7 in the cross-sectional view shows a modified form of the diaphragm element. In this embodiment, diaphragm 700 is formed of two elements 702 and 704 adhered to each other at their respective annular edge portions, with one end of a length of flexible tubing 110 fitted therebetween. Elements 702 and 704 are formed to have internal rims 706 and 708 which oppose each other and cooperatively locate opposite ends of a small internal biasing spring 710. Spring 710 may be made of any suitable material and should be sized to provide a gentle outwardly biasing force sufficient to cause the central portions of elements 702 and 704 to move away from each other when abdominal pressure abates.

The exact dimensioning, choice of materials, thickness of spring 710, etc., are all considered design details which persons in the ordinary skill in the mechanical arts should be able to select in light of the patient's needs.

With such a diaphragm 700, an increase in abdominal pressure acting over the relatively large external surface areas of elements 702 and 704 will cause compression of spring 701 and movement of the central portions of elements 702 and 704 towards each other. The resulting expulsion of pressurized fluid via flexible tubing 110 towards the urethra-constricting element should effect the desired urethra-constriction. Upon abatement of the external pressure spring 710 will expand outward and there will be a reduced pressure inside diaphragm 700. This will cause a return flow of the fluid back from the urethra-constricting element 102. The provision of a flow-control element 600 in such a system will cause the return flow to be relatively slow.

Figure 8:
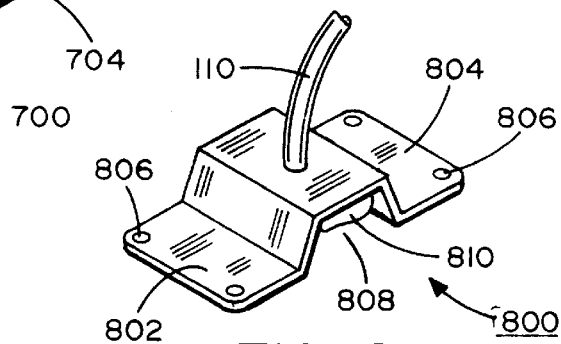
FIG. 8 is a perspective view of an alternative, non-planar, form of a base portion of the urethra-constricting element.

As mentioned earlier, it is not necessary that base 114 of urethra-constricting element 112 be flat. FIG. 8 illustrates an alternative form 600 of such a base. It comprises two substantial co-planar fixation portions 802 and 804, each provided with a plurality of apertures 806. A central recessed portion 808 is suitably sized to provide accommodation for fluid-receiving, flexible, expandable portion 810 of urethra-constricting element 800. This flexible expandable portion is in combination with flexible tubing 110 to receive pressurized fluid from the diaphragm (not shown) during use. Depending on the patient's personal circumstances, such an element may be preferable to the element 112 discussed earlier with particular reference to FIGS. 3A and 3B.

Figure 9A:
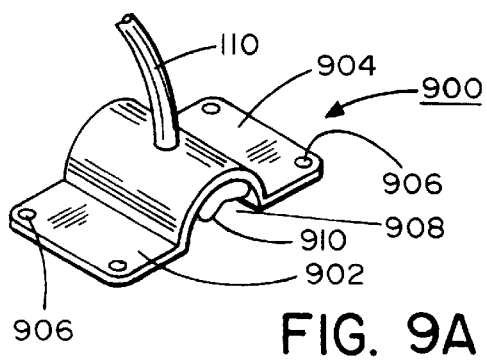
FIG. 9A is a perspective view of yet another non-planar base portion of the urethra-constricting element.

FIG. 9A illustrates in perspective view yet another alternative. Urethra-constricting element 900 has a base comprising two substantially co-planar portions 902, 904 provided with respective through apertures 906, with a central recessed portion defining a semi-cylindrical space 908 for accommodating the expandable portion 910 of the urethra-constricting element 900.

Figure 9B:
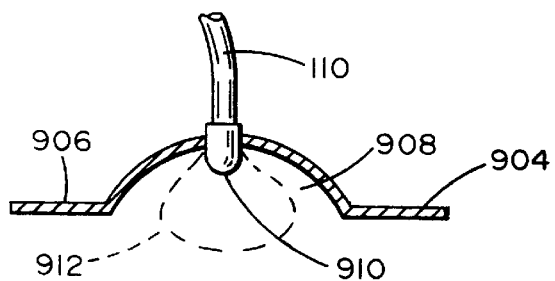
FIG. 9B is an end view of the urethra-constricting element per FIG. 9A fitted with an elastically expandable element for applying a constricting force to the urethra.

For certain patients, it may be desirable to form the pressure-responsive expandable portion 910 of an elastic material of a thickness and elasticity such that when the system is not subjected to ambient abdominal pressure it shrinks to a relatively small size easily contained within space 908, as best seen in FIG. 9B. Then, when abdominal pressure increases sufficiently to cause flow of pressurized flow via tubing 110, the elastic portion 910 will stretch and expand, as indicated by the broken lines in FIG. 9B, to take on an enlarged form 912. In this embodiment, the expandable portion 910 of the urethra-constricting element is not just flexible but is also elastically expandable. This elasticity inherently ensures that as soon as the abdominal pressure abates there will be an inherent tendency for elastic element 910 to return to its non-stretched shape and size and to return previously received fluid back to the diaphragm.

As persons of ordinary skill in the mechanical arts will readily appreciate, it may be desirable to provide a diaphragm 700 having an internal biasing spring 710, as discussed above with reference to FIG. 7, as well as an elastically stretchable portion 910 as illustrated and discussed above with reference to FIG. 9B. These two features, combined with a flow-control element 600 as discussed above with reference to FIGS. 5 and 6, should provide a responsive and highly effective continence-control system.

Figure 10A:
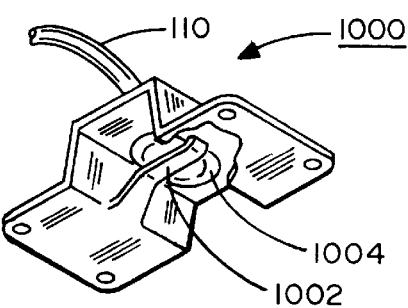
FIG. 10A is an upward perspective view of a modification of the urethra-constricting element base shown in FIG. 8, comprising a force-concentrating flexible base extension.

For certain patients it may be necessary to apply a significant local force to constrict the patient's urethra sufficiently. FIG. 10A in perspective form illustrates a form of base 1000 provided with a transverse, substantially central, elastic cantilever tongue 1002 pressing against the expandable portion 1004 which is to expand in response to an increase in abdominal pressure.

Figure 10B:
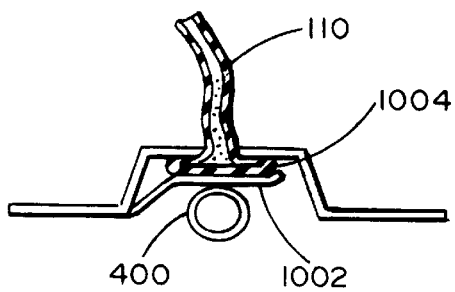
FIG. 10B is a partially-sectioned end view thereof with the flexible portion in an uninflated rest position.
Figure 10C:
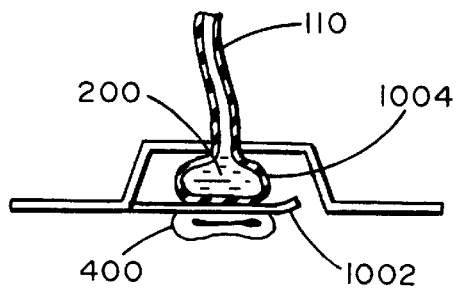
FIG. 10C is a similar view with the flexible portion in an inflated position.

As best seen with joint reference to FIGS. 10B and 10C, with such a structure the elastic tongue 1002 will press expandable portion 1004 against an inside surface of the base of the urethra-constricting element so as to force out therefrom some or all of the fluid initially present therein. This should be the situation when there is no increased abdominal pressure being experienced by the patient. Then, when there is an increase in the patient's abdominal pressure, and the diaphragm element of the system is compressed to force a corresponding flow of fluid through flexible tubing 110, entry of that pressurized fluid into the expandable/elastic portion 1004 will cause it to expand against the biasing force of tongue 1002. This is best seen in FIG. 10C.

As reference to FIG. 10A we will now make clear, the surface area of tongue 1002 that will press against urethra 400 can be made significantly smaller than the surface area of flexible/elastic portion 1004 which otherwise would have pressed on urethra 400 in an attempt to constrict the same. Thus, by reduction of the applied area, a force-concentration is obtained by which flexible/elastic portion 1004 of the urethra-constricting component acts on urethra 400 to close the same. Such a system may be highly responsive even to relatively small increases in abdominal pressure, and may permit the patient to perform a wider range of activities while being ensured that problem of stress incontinence will be effectively addressed. This may be important for patients who wish to perform physical exercises. Such a situation may be distinguished from the one in which a patient coughs, sneezes, or otherwise undergoes a virtually involuntary act resulting in an increase in abdominal pressure. It can thus be seen that the present invention, by appropriate sizing and selection of optional features, can be readily adapted to meet a variety of needs.

One preferred surgical procedure for implanting the device involves the formation of a transverse or mid-line incision in the lower abdominal area of the patient, to permit access into the patient's retropubic space. Following the initial incision, the surgeon incises the tissue and the anterior rectus facia. The rectus muscles are then separated in the mid-line, and a further sharp or blunt dissection allows access to the retropubic space 1100 or space of retzius. See FIG. 11. A Foley catheter positioned in the patient's bladder 1102 with a large inflatable balloon 1104 provided at the distal end thereof can be employed for easy identification of the bladder neck or urethrovesical junction by simple palpation by a finger of the surgeon's hand 1106 inserted vaginally. The urethra-constricting element 112 of the apparatus is then placed over the anterior surface of the proximal urethra 400 just below the bladder neck. It is then fixed to the muscular portion of the vaginal wall 1108 on opposite sides of the bladder neck, and may also optionally be affixed to the back of the symphysis pubis 1110. The urethra-constricting element 112 is then connected via flexible tubing 102 to the fluid-filled diaphragm 102 (or any of its variations) which is located in an intra-abdominal position where it can experience changes in abdominal pressure. The diaphragm 102 may be located in close proximity to the bladder 1102 and, if desired, may be fixed in position by suturing into surrounding tissue or by any other method of fixation.

Once the device has been appropriately located and affixed, it should be tested intra-operatively by applying a pressure on the diaphragm 102 to make certain that the urethra-constricting element 112 responds appropriately. If a flow-control element 600 has been included in the system, the surgeon at this stage should make certain that flows in opposite directions, per arrows "A" and "B" in FIG. 6, are as intended.

An endoscopic evaluation of the patient at this time would also be advantageous. Urethroscopy is performed to look at the urethra 400 from the inside to make certain that the urethra-constricting element 112 is appropriately located and acting when the device is actuated. Also, at this time, a cystoscopy may be performed to view the inside of the bladder 1102 and make certain that no inadvertent injury has occurred, that there is no inadvertent suture penetration, and that both ureters are functional.

If the laparoscopic surgery option has been selected, the necessary laparascopic insertion to obtaining access to the patient's retropubic space can be performed in known manner, e.g., laparoscopy with insufflation of the patient's abdominal cavity with carbon dioxide and sharp dissection into the retropubic space via a transperitoneal approach. In the alternative, an extra-peritoneal approach may be utilized, using either a conventional commercially available insufflation balloon or any other known technique to obtain access to the retro pubic space. Other techniques, e.g., utilizing a gasless approach or other insufflation media may also be considered and used as appropriate.

Once the retropubic space has been accessed, the surgeon may employ a Foley catheter in the patient's bladder to determine the precise location of the urethrovesicular junction or urethra where the urethra-constricting element is to be located.

As noted earlier, when the laparoscopic option is selected, the various elements may have to be initially rolled or folded tightly upon themselves so that each occupies a relatively small space and can be inserted via appropriately sized and located cannulae. The surgeon may normally position more than one cannula, and one of these may be used. The inserted elements are then connected to each other by suitable lengths of the flexible tubing 110, and the urethra-constricting element 112 (or any of the other options as discussed above) is then affixed to the vaginal tissue 1110 on opposite sides of the urethra 400 exactly as in the open incision technique. The surgeon may employ suturing clips, sutures 402, or any other elements for this purpose. The urethra-constricting element, in the alternative, may be affixed by clips, screws or the like to the symphysis pubis 1100. The diaphragm 102 and the flexible tubing 110, also passed through a suitable cannula, are then connected as discussed above. The inside space of the apparatus is then filled with the selected fluid via the injection valve component 120.

In order to determine exactly how much fluid to supply to the system, the surgeon may perform preliminary experiments with the patient to determine her normal intraabdominal pressure. The surgeon may then ask the patient to cough while her urethra is constricted by pressure applied digitally by the surgeon through the patient's vagina.

As will be readily appreciated by persons skilled in the type of specialized surgery involved, a certain degree of experience and judgment must guide the surgeon's decision on the length of flexible tubing 110, the manner of fixation of diaphragm 102 and urethra-constricting element 112, the amount of fluid to be filled in, whether to use open incision surgery or laparascopic surgery, and numerous other related factors.

Accordingly, a more precise specification of such details for present purposes is not deemed necessary.

With regard to the method according to this invention, as persons of ordinary skill in the mechanical and electromechanical arts and experienced in implantable devices will appreciate, the key is to sense an increase in intraabdominal pressure and to quickly apply a pressure to the urethra to thereby locally constrict it and prevent any leakage of urine. Obviously, apparatus to exercise the necessary detection of pressure and to generate the corresponding local force to temporarily constrict the urethra need not be solely mechanical, nor does it have to rely solely on hydrostatic principles. It is therefore to be understood that alternative elements of apparatus, including for example piezoelectric sensors/switches, electrical relays, electromagnetic solenoids to generate force, etc., may be adapted and substituted for the above-discussed exemplary elements in order to practice the method in its various aspects.

Obvious modifications and variations of the above-described structure and the manner of its use will no doubt occur to persons of ordinary skill in the art. All such obvious modifications and variations are intended to be comprehended within the present invention which is limited solely by the claims appended below.

What is claimed is:

1. An entirely implantable apparatus for controlling incontinence in a female, comprising:
    an inflatable element formed to automatically compress in response to an intraabdominal pressure increase during use and having a first opening;
    a length of flexible tubing, communicating at a first end with an interior of the inflatable element via said first opening; and
    a urethra-constricting element, comprising an inflatable portion having a second opening communicating with a second end of said flexible tubing, whereby said increase in intraabdominal pressure will inflate the inflatable portion against said female's urethra to automatically constrict the same.

2. The apparatus according to claim 1, further comprising:
    an injection valve communicating with the interior of the inflatable element, having a sealing portion formed to receive fluid via a hypodermic needle and to automatically seal when the hypodermic needle is removed.

3. The apparatus according to claim 2, further comprising:
    a predetermined quantity of a selected fluid, contained within the inflatable element, the flexible tubing and the urethra-constricting element.

4. The apparatus according to claim 3, further comprising:
    a flow control element connected to the flexible tubing to selectively control flow of the fluid at a first rate in a first direction from the inflatable element to the urethra-constricting element and at a second rate in a second direction from the urethra-constricting element to the inflatable element.

5. The apparatus according to claim 2, wherein:
    the urethra-constricting element comprises a securing portion formed to be internally secured adjacent a selected portion of a user's urethra with the inflatable portion thereby disposed to press against and squeeze the urethra when inflated.

6. The apparatus according to claim 5, further comprising:
a predetermined quantity of a fluid, contained within the inflatable portion, the flexible tubing and the urethra-constricting element.

7. The apparatus according to claim 6, wherein:
the inflatable element is formed so that, in a deflated state, it can be rolled into a small cylindrical shape laparoscopically insertable into a user's abdominal cavity.

8. The apparatus according to claim 2, wherein:
the urethra-constricting element comprises an elastic element locatable between the patient'urethra and the inflatable portion.

9. The apparatus according to claim 1, further comprising:
a predetermined quantity of a selected fluid, contained within the inflatable element, the flexible tubing, and the urethra-constricting element.

10. The apparatus according to claim 9, wherein:
the selected fluid is a sterile biocompatible liquid.

11. The apparatus according to claim 10, wherein:
the liquid is a saline solution.

12. The apparatus according to claim 9, further comprising:
a flow control element connected to the flexible tubing to selectively control flow of the fluid at a first rate in a first direction from the inflatable element to the urethra-constricting element and at a second rate in a second direction from the urethra-constricting element to the inflatable element.

13. The apparatus according to claim 1, wherein:
the inflatable element includes an element providing a biasing action for resisting compression of the inflatable element due to said intraabdominal pressure increase.

14. The apparatus according to claim 1, wherein:
the urethra-constricting element comprises a securing portion formed to be internally secured adjacent a selected portion of a user's urethra with the inflatable portion thereby disposed to press against and squeeze the urethra when inflated.

15. The apparatus according to claim 14, wherein:
the securing portion of the urethra-constricting element comprises a biasing element acting to bias the inflatable portion to an uninflated state.

16. The apparatus according to claim 14, further comprising:
means for securing the urethra-constricting element on opposite sides of the user's proximal urethra.

17. The apparatus according to claim 1, wherein:
the inflatable portion is elastically expandable.

18. The apparatus according to claim 1, wherein:
the inflatable element is formed so that, in a deflated state, it can be rolled into a small cylindrical shape laparoscopically insertable into a user's abdominal cavity.

19. The apparatus according to claim 18, wherein:
the securing portion of the urethra-constricting element comprises a biasing element acting to bias the inflatable portion to an uninflated state.

20. The apparatus according to claim 18, wherein:
the inflatable portion is elastically expandable.

21. The apparatus according to claim 1, wherein:
the urethra-constricting element comprises an elastic element locatable between the patient's urethra and the inflatable portion.

22. A method of controlling female incontinence, comprising the steps of:
forming an abdominal skin incision above the symphysis pubis of a female patient;
entering the patient's retropubic space through the incision and identifying an anatomic location of the user's bladder neck;
fixing, on opposite sides of the proximal urethra and bladder neck, a urethra-constricting element comprising an inflatable portion communicating with one end of a length of flexible tubing; and
in communication with another end of said tubing providing an inflatable element that is compressible in response to an intraabdominal pressure increase and is placed at a selected location such that when the inflatable element is subjected to an increase in intraabdominal pressure it will automatically compress to transfer a selected fluid via said tubing to the inflatable portion of the urethra-constricting element to thereby cause the urethra-constricting element to expand against an immediately adjacent portion of the urethra to squeeze and constrict the urethra threat.

23. The method according to claim 22, comprising the further step of:
selectively extracting from or adding to the selected fluid contained within the mutually communicating inflatable element, flexible tubing and urethra-constricting element, whereby the responsiveness of the urethra-constricting element is adjusted to said patient's particular needs.

24. The method according to claim 22, wherein:
the urethra-constricting element comprises an elastic element locatable between the patient's urethra and the inflatable portion.

25. A method of controlling incontinence in a female patient, comprising the steps of:
forming an entrance into the patient's retropubic space;
identifying the patient's bladder neck; and
through the entrance, locating in the retropubic space a fluid-containing inflatable element communicating via a flexible tubing with a urethra-constricting element having an inflatable portion positioned adjacent a selected portion of the patient's urethra adjacent the bladder neck,
whereby an increase in the patient's abdominal pressure will cause compression of the inflatable element, transmission of a pressurized flow of a fluid via the tubing, and a corresponding expansion of the inflatable portion of the urethra-constricting element to cause the urethra-constricting element to press against the selected portion of the patient's urethra and squeeze the same to thereby impede urine flow therethrough.

26. The method according to claim 25, wherein:
the step of locating the inflatable element comprises the steps of initially deflating the inflatable element, rolling it tightly into a small cylindrical form, and introducing it through a cannula to a selected location in the patient's abdomen; and
injecting a suitable quantity of the fluid into the inflatable element.

27. The method according to claim 26, comprising the further step of:
securing the urethra-constricting element by affixation thereof to the patient's tissue adjacent the urethra.

28. The method according to claim 27, wherein:

the securing step comprises at least one of suturing to soft tissue and affixation to bone.

29. The method according to claim 25, wherein:

the urethra-constricting element comprises an elastic element locatable between the patient's urethra and the inflatable portion.

30. A method of controlling female incontinence, comprising the steps of:

sensing an increase in the female's abdominal pressure;

communicating the increased pressure to a selected location on the female's urethra; and applying the increased pressure to solely thereby constrict the female's urethra at the selected location.

31. A method of controlling female incontinence, comprising the step of:

placing within the patient's retropubic space a compressible fluid-filled diaphragm element communicating via a flexible tubing with a urethra-constricting element having an expandable portion positioned adjacent a selected portion of the patient's urethra near the patient's bladder neck;

whereby an increase in the patient's abdominal pressure will cause compression of the diaphragm element and expulsion therefrom of a corresponding flow of fluid via the tubing, and a corresponding expansion of the expandable portion against an adjacent portion of the urethra will thereby squeeze and temporarily constrict the urethra thereat to impede urine flow therethrough.

32. The method according to claim 31, comprising the further step of:

providing an elastic element between the expandable portion and the adjacent portion of the urethra, whereby the expandable portion transmits a force via the elastic element to the adjacent portion of the urethra.

* * * * *